United States Patent
Wang et al.

(10) Patent No.: US 6,522,714 B1
(45) Date of Patent: Feb. 18, 2003

(54) ROW-WISE FULL HELICAL VIEW WEIGHTING METHOD AND APPARATUS FOR CT SCANNERS

(75) Inventors: Sharon Wang, Brookfield, WI (US); Stephen Metz, Greenfield, WI (US); Thomas Toth, Brookfield, WI (US); Piero U. Simoni, New Berlin, WI (US); Jianying Li, New Berlin, WI (US)

(73) Assignee: GE Medical Systems Global Technologies Company LLC, Waukesha, WI (US)

( * ) Notice: Subject to any disclaimer, the term of this patent is extended or adjusted under 35 U.S.C. 154(b) by 9 days.

(21) Appl. No.: 10/037,032

(22) Filed: Nov. 9, 2001

(51) Int. Cl.$^7$ ................................. A61B 6/03
(52) U.S. Cl. ..................... 378/15; 378/19; 378/901
(58) Field of Search ................... 378/4, 8, 15, 901, 378/19, 9

(56) References Cited

U.S. PATENT DOCUMENTS 5,396,418 A * 3/1995 Heuscher ................ 378/15

* cited by examiner

*Primary Examiner*—David V. Bruce
(74) *Attorney, Agent, or Firm*—Quarles & Brady, LLP; Carl Horton (57) ABSTRACT

A method and apparatus for performing image reconstruction using data obtained by an N beam helical scan, the method including generating projection data arrays for each of the N row in a CT detector, weighting the data arrays using a unique weighting function that is applicable to detectors having many different numbers of rows N to generate helical weighted arrays for each row, weighting the helical weighted arrays by applying a conjugate weighting function to generate conjugate arrays for each detector row and then combining the conjugate weighted arrays, filtering and back-projecting to generate a slice image.

20 Claims, 6 Drawing Sheets

ROW-WISE FULL HELICAL VIEW WEIGHTING METHOD AND APPARATUS FOR CT SCANNERS

STATEMENT REGARDING FEDERALLY SPONSORED RESEARCH

Not applicable.

CROSS-REFERENCE TO RELATED APPLICATIONS

Not applicable.

BACKGROUND OF THE INVENTION

The present invention relates to multi-slice helical computerized tomography and more particularly to a tomography algorithm, method and apparatus which reduces the data acquisition time and data processing time required to generate an image while maintaining high image quality.

In computerized tomography (CT) X-ray photon rays are directed through a patient toward a detector. Attenuated rays are detected by the detector, the amount of attenuation indicative of the make up (e.g. bone, flesh, air pocket, etc.) of the patient through which the rays traversed. The attenuation data is then processed and back-projected according to a reconstruction algorithm to generate an image of the patient's internal anatomy. Generally, the "back-projection" is performed in software but, as the name implies, is akin to physically projecting rays from many different angles within an image plane through the image plane, the values of rays passing through the same image voxels being combined in some manner to have a combined effect on the voxel in the resulting image. Hereinafter the data corresponding to rays which are back-projected will be referred to as back-projection rays.

During data acquisition, if a patient moves, artifacts can occur in the resulting image which often render images useless or difficult to use for diagnostics purposes. For this and other reasons the CT industry is constantly trying to identify ways to reduce the duration of acquisition periods without reducing the quality of the data acquired.

Various CT system features and procedures have been developed to increase data acquisition speed. Some of the more popular features and procedures including fan beam acquisition, simultaneous multiple slice acquisition, helical scanning and half-scanning. In fan beam acquisition the source is collimated into a thin fan beam which is directed at a detector on a side opposite a patient. In this manner, a complete fan beam projection data set is instantaneously generated for a beam angle defined by a central ray of the source fan beam. The source and detector are rotated about an image plane to collect data from all (e.g., typically 360 degrees) beam angles. Thereafter the collected data is used to reconstruct an image in the image plane. Thus, fan beam acquisition reduces acquisition period duration.

With respect to half-scanning, assuming a patient remains still during a data acquisition period, conjugate data acquisitions (i.e., data acquired along the same path from opposite directions) should be identical. In addition, using a fan beam, at least one ray can be directed through an image plane from every possible beam angle without having to perform a complete rotation about the patient. To this end, as known in the industry, data corresponding to every beam angle associated with a single image plane can be collected after a $(\pi+2\gamma)/2\pi$ rotation about the patient where $\gamma$ is the fan beam angle. Because less than an entire rotation about a patient is required to acquire data corresponding to a slice image, these acquisition methods and systems are generally referred to as half-scan methods and systems. Thus, half-scan acquisition has been employed to reduce acquisition period duration in conjunction with single row detectors.

Single slice detectors, fan beams and half-scans can be used to generate data in several different parallel image planes which, after data acquisition, can be used by a processor to generate an image anywhere between the image planes through interpolation/extrapolation procedures known in the art. For example, assume that during two data acquisition periods first and second data sets were acquired which correspond to first and second parallel acquisition planes, respectively, the planes separated by 0.25 inches. If a user selects an image plane for reconstructing an image which resides between the first and second acquisition planes, interpolation between data in the first and second sets can be used to estimate values of data corresponding to the selected image plane. For instance, assume that, among other rays, during the acquisition periods a first ray and a second ray were used to generate data in the first and second sets, respectively, and that the first and second rays were parallel (i.e. had the same beam and fan angles). In this case, by interpolating between the data acquired from the first and second rays generates an estimated value corresponding to a hypothetical back-projection ray which is parallel to the first and second rays and which is within the image plane. By performing such interpolation to generate back-projection rays for every beam and fan angle through the image plane a complete data set corresponding to the image plane is generated.

While such systems work, unfortunately, the acquisition time required to generate data corresponding to many image planes is excessive and inevitable patient movement often causes image artifacts.

One way to speed up data acquisition corresponding to several image planes is by employing a multi-row detector with a fan beam. In multi-row detector systems, a relatively thick fan beam is collimated and directed through a patient at a multi-row detector, each detector row in effect gathering data for a separate "slice" of the thick fan beam along the Z or translation axis perpendicular to a fan beam width. Despite each detector row having a thickness, in these systems it is assumed that the detected signals in each row correspond to a plane centered within the row as projected onto the isocenter Z. Hereinafter the central plane through a row will be referred to as a row center.

After data acquisition an interface enables a system user to select an image plane from within the area corresponding to the collected data. The selected image plane is between the row centers of at least two adjacent detector rows. After image plane selection, a processor interpolates between data corresponding to adjacent rows to generate back-projection rays corresponding to the selected image plane. When another image corresponding to a different image plane is desired, after selecting the plane, the processor again identifies an acquired data subset for interpolation, additional processing and back-projection. Thus, multi-row detector systems further reduce data acquisition period duration where several image planes may be selected for reconstruction.

One limitation with multi-row detectors is that, during a single acquisition period, data can only be collected which corresponds to the detector thickness. To collect additional data corresponding to a greater patient volume or region of interest (ROI), after one acquisition period corresponding to a first volume, the patient has to be moved along a translation axis until a second volume which is adjacent the first volume is between the source and detector. Thereafter a second acquisition process has to be performed. Similarly, to collect additional data corresponding to a third volume the patient has to be transported to another relative location with respect to the source and detector. Required translation without acquisition necessarily prolong the acquisition period and the additional acquisition time and aligning processes inevitably result in relative discomfort, additional patient movements and undesirable image artifacts.

Helical scanning systems have been developed so that data can be collected during a single acquisition period without halting patient translation during the acquisition period. In a helical scanning system, the source and detector array are mounted on opposing surfaces of an annular gantry and are rotated there around as a patient is transported at constant speed through the gantry. The X-ray beam sweeps a helical path through the patient, hence the nomenclature "helical scanning system". Data acquisition can be sped up by increasing operating pitch (i.e., table translation speed relative to gantry rotation rate). After data is acquired the data is processed to generate back-projection ray estimates and account for data nuances which are caused by the helical acquisition.

Various combinations of the fan-beam, multi-slice, half-scan and helical scanning features have been combined to realize synergies and have been somewhat successful. For example, one system combines a multi-row fan beam detector and a fan beam source with a helical scanning procedure to rapidly acquire imaging data using a high pitch/high speed mode of operation. For example, U.S. Pat. No. 5,541, 970 (hereinafter "the '970 patent") which issued on Jul. 30, 1996 and is entitled "Image Reconstruction for a CT System Implementing Four Fan Beam Helical Scan" teaches an exemplary system including a four row detector where, during acquisition, helical data is collected about an ROI for each of the four rows. The collected data includes "views" where each view includes the data corresponding to the entire detector that is collected from a specific source angle about the gantry. Hereinafter, the phrase "row view" will be used to identify the data corresponding to a specific detector row acquired at a specific gantry angle so that a four row detector will have first, second, third and fourth separate row views at each gantry angle.

After data has been collected and stored, when a system operator identifies a transaxial plane through the ROI at which a required image is to be generated, a system processor selects a sub-set of the helical data (hereinafter "a selected data subset") which is, in effect, centered on the selected plane. Thereafter, the selected data sub-set is altered to generate slice image data corresponding to the slice image plane, the altered data is filtered and back-projected across the slice image plane to generate the desired image for viewing and further processing. In order to generate a high quality image, the back-projected data must include views from many equi-spaced gantry angles about the slice plane.

In order to convert the selected data sub-set into slice image data for filtering and back-projection, the selected data sub-set including data from all four detector rows is weighted according to an algorithm that is spatially dependent along the Z or translation axis. To this end, for each detector row, at least one row view will typically be aligned with the slice image plane and therefore can be used for imaging purposes in its acquired state (i.e., without weighting). Hereinafter the gantry angle corresponding to an aligned row view will be referred to as an aligned angle.

For each remaining gantry angle in the slice image plane there are other row views within the selected data sub-set proximate the imaging plane. For instance, in the case of a four row detector, for gantry angles that are similar to the aligned angle, the selected data set will include two row views preceding the image plane and two row views following the image plane. For other gantry angles that are less similar to the aligned angle the selected data set will include either one row view preceding the image plane and three row views following the image plane or vice versa.

In any event, for each remaining gantry angle (i.e., all gantry angles that are not aligned with the slice image plane) in the slice image plane, the proximate row views are weighted generally as a function of spacing along the Z-axis. For instance, for a given gantry angle where the slice image plane is between second and third detector row views and is closer to the second row view than the third row view, the row view weightings from highest to lowest are second, third, first and fourth, respectively. After each row view within the selected data sub-set is weighted, the weighted data is filtered and back-projected to generate the required image. In this manner, a full set of weighted views is created to perform a conventional 360° CT reconstruction.

While the algorithm described in the '970 patent works well for four row detectors, unfortunately, when larger detectors are designed to collect additional rows of data (e.g., eight row detectors), it has been found that a higher helical pitch (i.e., table translation speed relative to gantry rotation rate) and larger cone angles (i.e., the angles between X-ray beams within the Z or translation axis) result which cause image artifacts and appreciably adversely affect the diagnostic value of resulting images.

SUMMARY OF THE INVENTION

The present invention includes a new weighting algorithm and method that can be used with detectors having virtually any number of detector element rows to generate highly accurate images from helically scanned CT data. The inventive algorithm generally includes two sequential weighting processes. First, after helically scanned data has been collected for a region of interest (ROI) and a transaxial slice image plane through the ROI has been identified, a sub-set of data corresponding to the selected slice image plane is identified and then a helical weighting algorithm is applied separately to the data corresponding to each of the detector rows to generate a separate helical weighted array for each detector row. For instance, where a detector includes eight detector rows, eight separate helical weighted arrays are generated.

Figure 5:
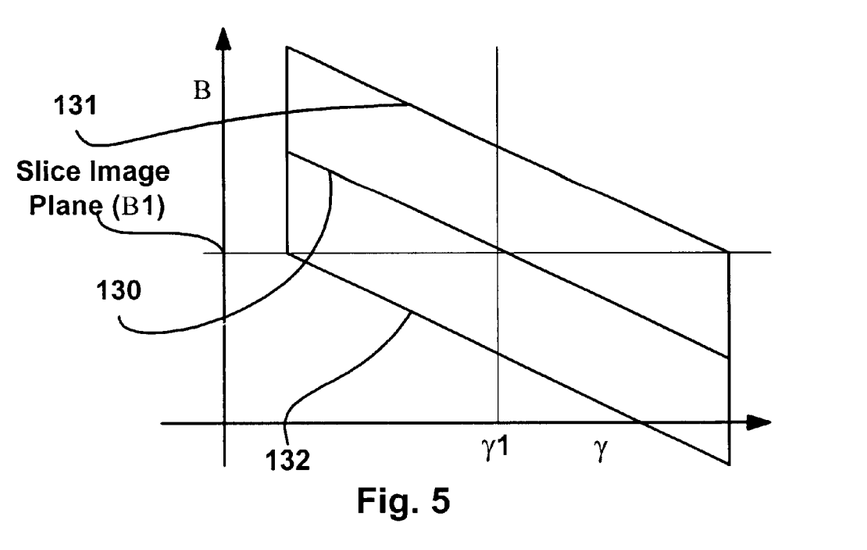
FIG. 5 is a graph illustrating an exemplary weighting algorithm in two dimensions that is applied on a detector row by row basis according to the present invention.

Importantly, referring to FIG. 5 where an exemplary inventive weighting function is illustrated in two dimensions, the inventive weighting function applied to each row view is both gantry angle $\beta$ and beam angle $\gamma$ dependent. To this end, along line 130 the weighting function has a value of one, along each of lines 131 and 132 the weighting function has a value of zero and between lines 131 and 130 and lines 132 and 130 the weighting function slopes from zero to one. The slope of lines 130, 131 and 130 is referred to generally as a tangent weighting parameter $t_g$ which, after system pitch and detector width are set, can be modified through an optimization process until optimal imaging characteristics result (e.g., artifacts and noise are minimized).

Second, after the helical weighting function has been applied and helical weighted arrays for each row have been generated, a conjugate weighting function is applied to each helical weighted array thereby generating a separate conjugate weighted array for each detector row.

After conjugate weighting is applied the resulting conjugate weighted arrays are filtered and back-projected thereby generating a slice image corresponding to the selected slice image plane. The conjugate weighted arrays may be combined before filtering and back-projection or the filtering and back-projection may be performed on a row by row basis to generate row specific slice images which are then combined to generate a final or combined slice image.

These and other aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

DESCRIPTION OF THE PREFERRED EMBODIMENT

A. Hardware

Figure 1:
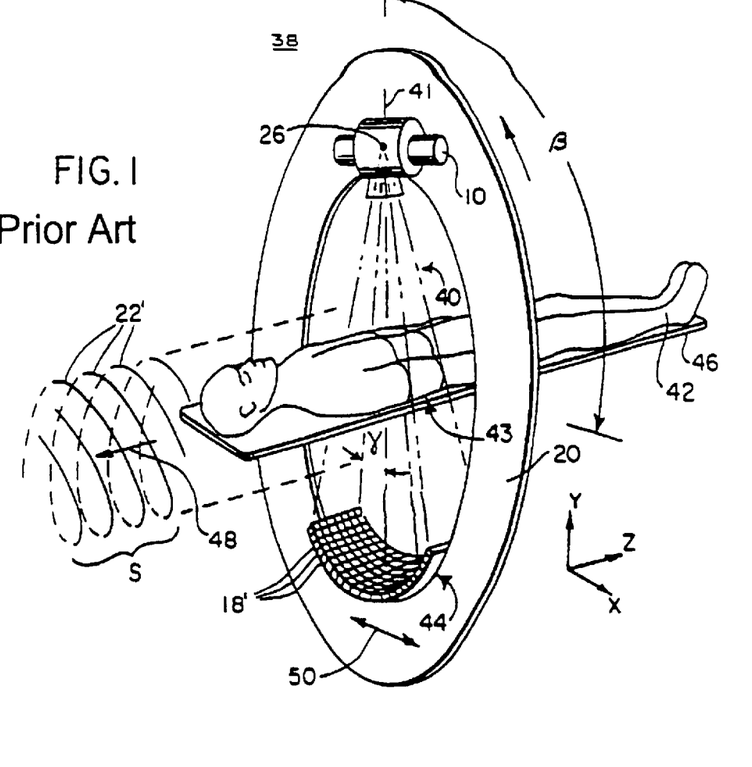
FIG. 1 is a perspective view of a CT apparatus used to practice the present invention which includes a detector array having rows and columns of detector elements and fan beam source.

Referring now to FIG. 1, a CT scanner for use with the present invention includes a gantry 20 having an opening (i.e., defining an imaging area) supporting an x-ray source 10 oriented to project a fan beam 40 of x-rays along the beam axis 41 through a patient 42 to a supported and opposed detector array 44. The gantry 20 rotates to swing the beam axis within a gantry plane 38 defining the x-y plane of a Cartesian coordinate system. Rotation of the gantry 20 is measured by beam angle B from an arbitrary reference position within the gantry plane 38.

A patient 42 resets on a table 46 which may be moved along a translation axis 48 aligned with the Z-axis of the Cartesian coordinate system. Table 46 crosses gantry plane 38 and is radio-translucent so as not to interfere with the imaging process.

Figure 3:
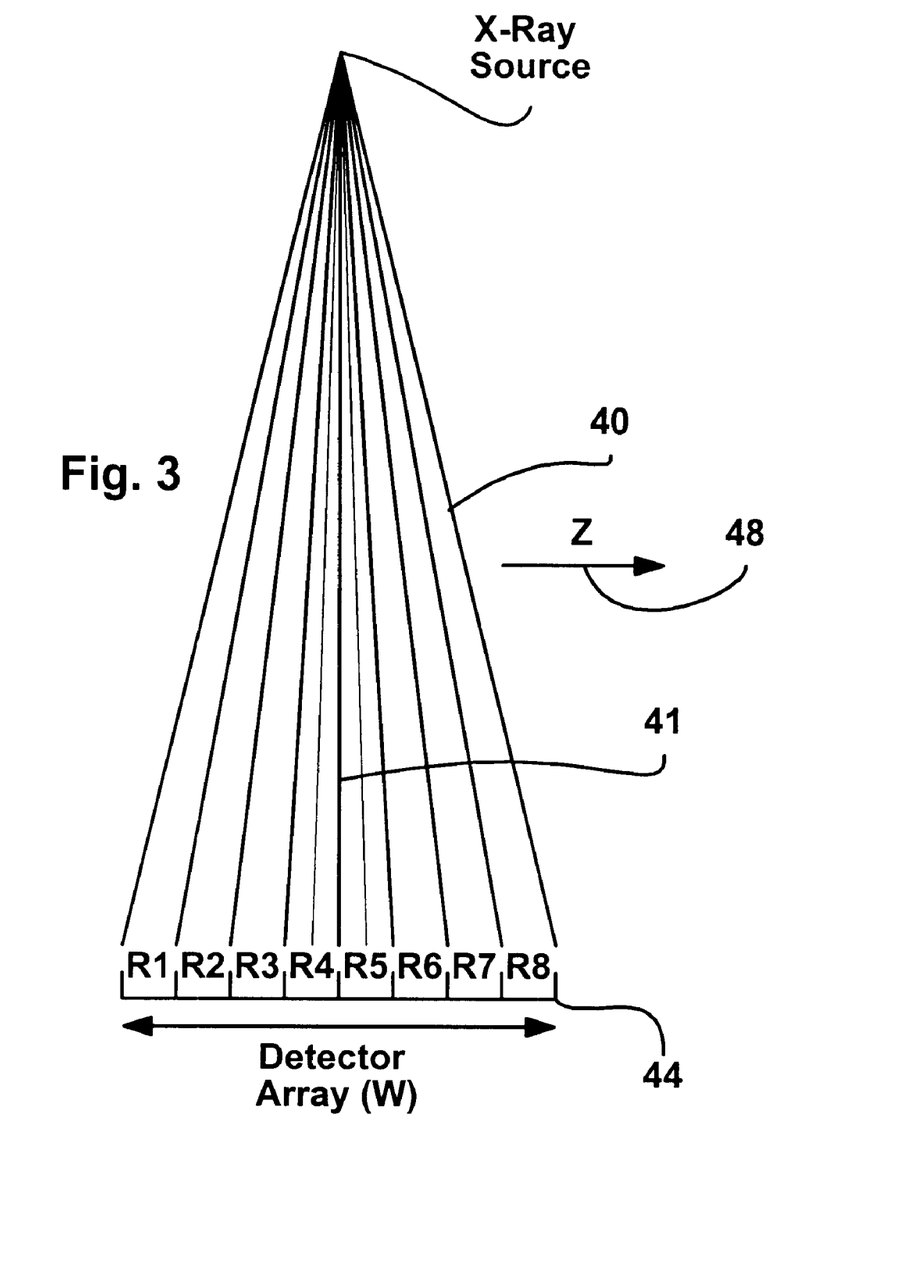
FIG. 3 is a schematic diagram illustrating an X-ray source and an eight row detector that divides the source beam into eight separate radiation beams.

The x-rays of the fan beam 40 diverge from the beam axis 41 within the gantry plane 38 across a transverse axis 50 generally orthogonal to both the beam axis 41 and the translation axis 48 at a fan beam angle γ. Referring also to FIG. 3, the x-rays of beam 40 also diverge slightly from the beam axis 41 and the gantry plane 38 across the Z-axis 48. A maximum beam angle γ is identified hereinafter by symbol Γ.

After passing through patient 42, the x-rays of the fan beam 40 are received by detector array 44 which includes a plurality of detector elements 18'. Referring also to FIG. 3, detector elements 18' in exemplary array 44 are arranged in eight rows R1 through R8 (i.e., array 44 is an eight slice detector) extending along the traverse axis 50 that subdivide array 44 along the Z-axis and a plurality of columns extending along Z-axis 48. The width W of detector array 44 is measured along Z-axis 48. The surface of detector array 44 may be planar or may follow a section of a sphere or cylinder having a center at focal spot 26 or alternatively at the system isocenter.

The detector elements 18' each receive x-rays and provide intensity measurements along separate rays of the fan beam 40. Each intensity measurement describes the attenuation via a line integral of one fan beam ray passing through a portion of volume 43 of patient 42. The dimension of volume 43 along Z-axis 48 is greater than the Z-axis width of eight slice array 44.

Figure 2:
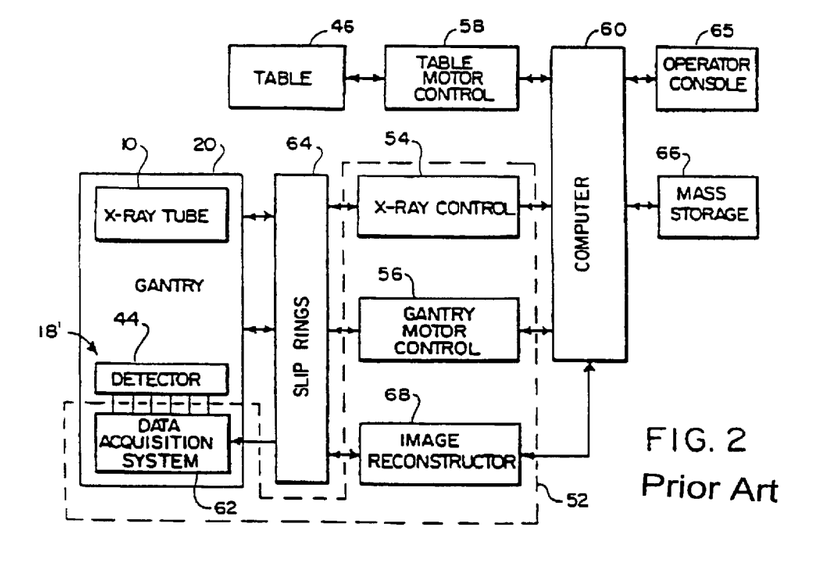
FIG. 2 is a block diagram of CT control system which may be used to control the CT apparatus of FIG. 1 and which is useful for the purposes of practicing the present invention.

Referring to FIGS. 1 and. 2, an exemplary control system for controlling the CT imaging system of FIG. 1 includes gantry associated control modules collectively identified by numeral 52, a table motor control 58, slip rings 64, a central processing computer 60, an operator's console 65 and a mass storage device 66. Modules 52 include an x-ray control 54, a gantry motor control 56, a data acquisition system 62 and an image reconstructor 68. X-ray control 54 provides power and timing signals to the x-ray source 10 to turn it on and off as required under the control of a computer 60. Gantry motor control 56 controls the rotational speed and position of the gantry 20 and provides information to computer 60 regarding gantry position. Data acquisition system 62 samples and digitizes intensity signals from the detector elements 18' of detector array 44 provides the digitized signals in the form of helical data row views to computer 60 for storage in mass storage device 66. Reconstructor 68 is linked to computer 60 for receiving data there from and weighting the data according to the inventive method, filtering the weighted data and back-projecting the data to, as its label implies, construct a slice image for viewing.

Each of the above modules is connected to associated gantry mounted components via slip rings 64 and is also linked to computer 60 for control purposes Slip rings 64 permit gantry 20 to rotate continuously through angles greater than 360° to acquire projection data.

The speed and position of table 46 along translation axis 48 is controlled by computer 60 by means of table motor control 58. Computer 60 receives commands and scanning parameters via operator console 65 that generally includes some type of visual interface device (e.g., a CRT display) and one or more input devices (e.g., a keyboard, a mouse controlled display cursor, etc.). Console 65 allows an operator to enter parameters for controlling a data acquiring scan and to display constructed image and other information from computer 60.

Mass storage device or memory 66 provides a means for storing operating programs for the CT imaging system, as well as image data for future reference by the operator. Both computer 60 and the image reconstructor 68 have associated electronic memory (not shown) for storing data and pulse sequencing programs.

In operation, gantry motor control 56 brings gantry 20 up to a rotational speed and table motor control 58 begins translation of table 46 along translation axis 48. The x-ray control 54 turns on x-ray source 10 and projection data is acquired on a continuous basis. The table 46 translation speed relative to the gantry rotation rate is referred to as the operating "pitch". At each beam angle B, the projection data acquired comprises intensity signals corresponding to each detector element 18' at each particular column and row of array 44. The collected data is stored in storage device 66 as helical data including row views correlated to gantry angles.

Referring again to FIG. 3, the eight rows R1–R8 of detectors 44 define in an eight fan beam system. The x-ray fan beam 40 is, in effect, split into eight fan beams displaced along the Z-axis.

Referring now to FIGS. 1 through 4, image reconstructor 68 includes a summer 118 a filter and back-projector 116 and separate processing circuitry assemblies for each of the detector rows R1 through R8, the separate assemblies identified by labels 100(R1) through 100(R8), respectively. Each of assemblies 100(R1) through 100(R8) is essentially identical and operates in a similar fashion and therefore, in the interest of simplifying this explanation, only circuitry assembly 100(R1) is explained here in detail. It should suffice to say here that assembly 100(R1) processes data row views generated by row R1 of detector array 44, assembly 100(R2) processes data row views generated by row R2 of array 44, and so on, and that array output signals of assemblies 100(R1) through 100(R8) are provided to summer 118 which adds the array signals to generate weighting data views within a selected slice image plane that can be filtered and back-projected to generate an image corresponding to the image plane.

Figure 4:
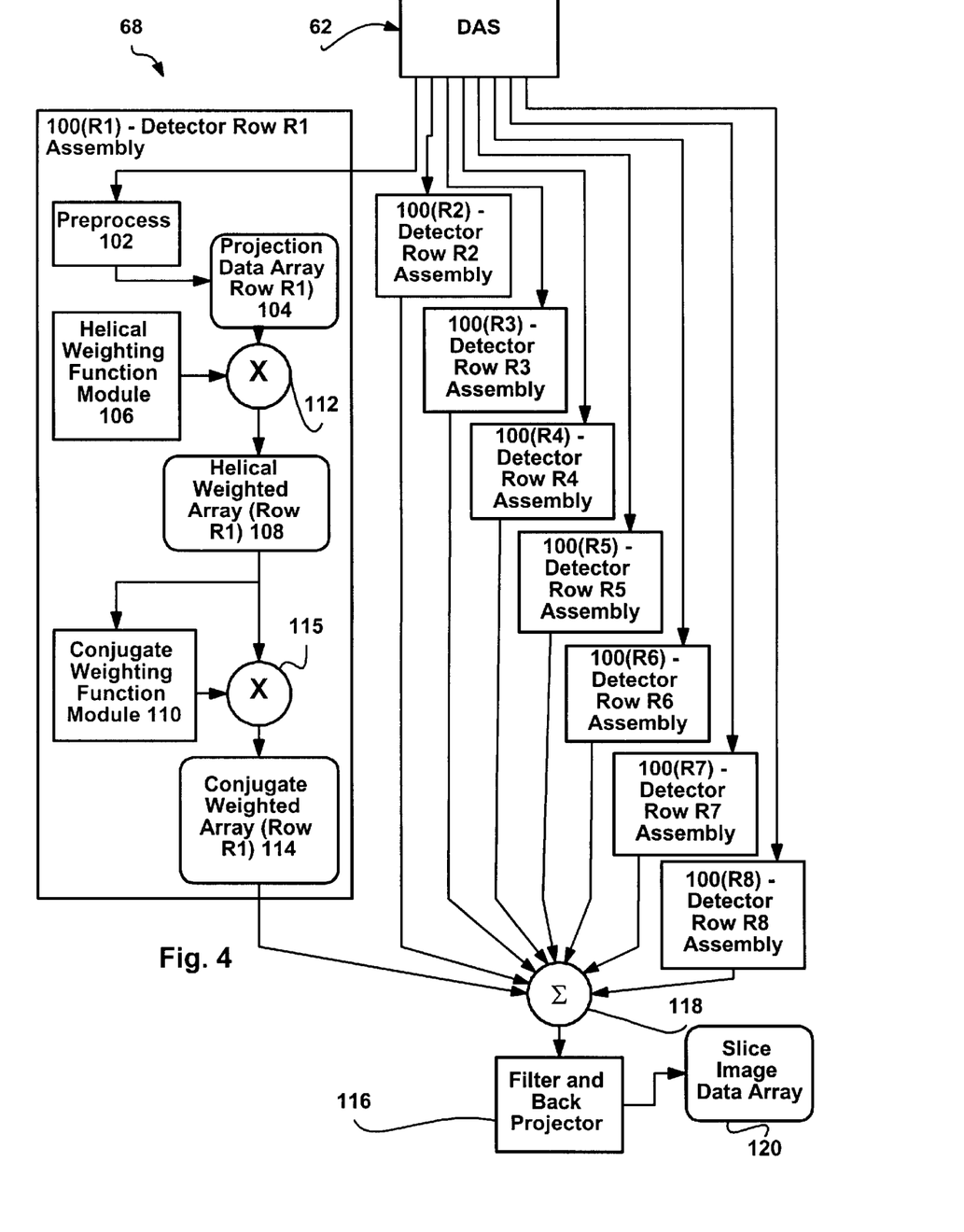
FIG. 4 is a schematic diagram illustrating an exemplary image reconstructor according to the present invention.

Referring to assembly 100(R1), assembly 100(R1) includes a preprocessor 102, first and second multipliers 112 and 115, respectively, a helical weighting function module 106 and a conjugate weighting function module 110. Assembly 100(R1) components receive row views corresponding to detector row R1 and alter the received views several times to generate intermediate data arrays, the end result being a conjugate weighted array 114 corresponding to row R1. In FIG. 4, to distinguish data arrays from assembly 100(R1) components, the arrays are identified by blocks having rounded edges while assembly components are identified by blocks having sharp angles. The intermediate arrays include a projection data array 104 and a helical weighted array 108.

Referring still to FIGS. 2 and 4, each row view of data from DAS 62 for corresponding to detector row R1 is provided to preprocessor 102 where the view data is preprocessed to correct for various well-known errors such as beam hardening, offsets and variations in detector and channel gain. In addition, preprocessor 102 generates the negative logarithm of the view to provide projection data which is stored as the projection data array 104.

The projection data array 104 is read out and the helical weighting function generated by module 106 is applied to the projection data array 104 by multiplier 112 thereby generating the helical weighted array 108 which is again stored. The helical weighted array 108 is read out and the conjugate weighting function generated by module 110 is applied to the helical weighted array 108 by multiplier 115 thereby generating the conjugate weighted array 114 which is once again stored.

The conjugate weighted array 114 is provided to summer 118 along with similar arrays from assemblies 100(R2) through 100(R8). The arrays are summed by summer 118 to generate a combined slice plane data array. The combined array is provided to filter-back-projector 116 which filters and back-projects-the combined array views to produce the slice image 120. The resulting slice image array 120 is stored in device 66 for later use or may be displayed to the operator via console 65.

In the alternative, instead of summing the conjugate weighted arrays prior to filtering and back-projecting, each conjugate weighted array may be separately filtered and back-projected to generate separate image data arrays for each row. Thereafter, the separate image data arrays may be summed on a pixel-by-pixel basis to generate the combined and final slice image array 120.

B. Weighting Processes

The present invention, in one form, relates specifically to the creation of weighted projection data arrays 108 and conjugate weighted projection arrays 114. In this regard, an inventive method generally includes two separate sub-processes including a helical weighting process and a conjugate weighting process. These two processes will be described sequentially. With respect to the following discussion, label d denotes the detector row spacing measured (i.e., the z-axis spacing) at the axis of gantry rotation 48, s denotes the table feeding speed per gantry rotation, and pitch p denotes the ratio of d and s such that:

1. Helical Weighting Process

Referring now to FIG. 5, a universal row specific weighting function according to the present invention is graphically illustrated in two dimensions. In FIG. 5, as labeled, gantry angle $\beta 1$ corresponds to a selected slice image plane within which an image is to be generated. Lines 130, 131 and 132 correspond to one, zero and zero weighting values, respectively, with the region between lines 131 and 130 ramping from zero to one and the region between lines 132 and 130 similarly ramping from zero to one. Thus, it is clear from a quick perusal of FIG. 5 that, according to the inventive weighting algorithm, the weight values vary as a function of both the gantry angle $\beta$ and the fan angle $\beta$ within specific row views (i.e., within a view corresponding to a specific gantry angle $\beta$). Thus, for instance, for the row view corresponding to gantry angle $\beta 1$ within the selected image plane, a central ray $\beta 1$ has a weight value of one while other rays within the row view have weights between one and zero (i.e., between lines 130 and either 131 or 132 as illustrated). Pitch p and detector width are typically selected. Line 130 slope clearly affects the weighting function and therefore is extremely important and is set during an optimization commissioning process wherein a tangent weighting parameter $t_g$ is adjusted to alter the slope until optimal imaging characteristics result (e.g., noise and artifacts are minimized).

The helical weighting factor illustrated in FIG. 5 can be generically expressed according to the following equations:

$$w_r(\beta, \gamma) = \begin{cases} 0, & \beta > \beta_{r3} \\ 1 - \dfrac{\beta - \beta_{r2}}{\Delta\beta}, & \beta_{r1} \geq \beta > \beta_{r2} \\ 1 + \dfrac{\beta - \beta_{r2}}{\Delta\beta}, & \beta_{r2} \geq \beta \geq \beta_{r1} \\ 0, & \beta < \beta_1 \end{cases} \quad \text{Eq. 2}$$

where, $$\Delta\beta \dfrac{2\pi}{p}, \text{ and } p \text{ is the helical pitch,} \quad \text{Eq. 3}$$

$$\beta_{r1} = t_g\gamma + r\Delta\beta; \quad \text{Eq. 4}$$

$$\beta_{r2} = \beta_{r1} + \Delta\beta, \text{ and} \quad \text{Eq. 5}$$

$$\beta_{r3} = \beta_{r1} + 2\Delta\beta. \quad \text{Eq. 6}$$

where $\beta$ is a gantry angle centered on the selected imaging plane and central within the data corresponding to a specific row, and r is the detector row which ranges from zero to N−1 where N is the number of rows in a detector 44.

It is instructive in understanding the helical weighting algorithm corresponding to Equations 2 through 5 above to view the sum of the helical weights for all eight detector rows determined via Equations 2 through 5 above at each gantry angle and each fan angle. To this end, assuming approximately 888 fan angles γ per view and 984 separate gantry angles, referring now to FIGS. 6 and 7, three dimensional and two dimensional graphs of the summed detector weights for each gantry angle β and each fan angle γ determined according to Equations 2 through 5 are illustrated, respectively. For instance, the summed weights for the gantry and phase angles within region 140 is one. Similarly, the summed weights for the gantry and phase angles within regions 146 and 148 is zero while the summed weights for the gantry and phase angles within regions 142 and 144 ramp from zero to one between regions 146 and 148 and region 140, respectively. Clearly the illustrated summed weighting function is unique.

2. Conjugate Weighting Process

Where the acquisition system is run at a high helical pitch the data corresponding to the selected image slice plane corresponds to less than 2π gantry rotations about an ROI and therefore it is not possible to reconstruct an accurate image directly using only the helically weighted arrays. Additional weighting has to be performed. To this end, a conjugate weighting function has been developed that can be expressed by the following equations:

$$w_c(\beta, \gamma) = \begin{cases} 1 - w_n, & \beta_{nc} \leq \beta < \beta_{nc} + \Delta\beta \\ 2, & \beta_{nc} + \Delta\beta \leq \beta < \beta_{n0} - \Delta\beta \\ 1 - w_0, & \beta_{n0} - \Delta\beta \leq \beta \leq \beta_{n0} \end{cases} \quad \text{Eq. 7}$$

where $w_0$ and $w_n$ are helical weighting functions for the first and last detector rows (e.g., R1 and R8 in FIG. 3), and $\beta n_0$ and $\beta n_c$ are the conjugate parameters (i.e., gantry angles) corresponding to the beginning of the first row and the end of the last row, respectively.

Figure 6:
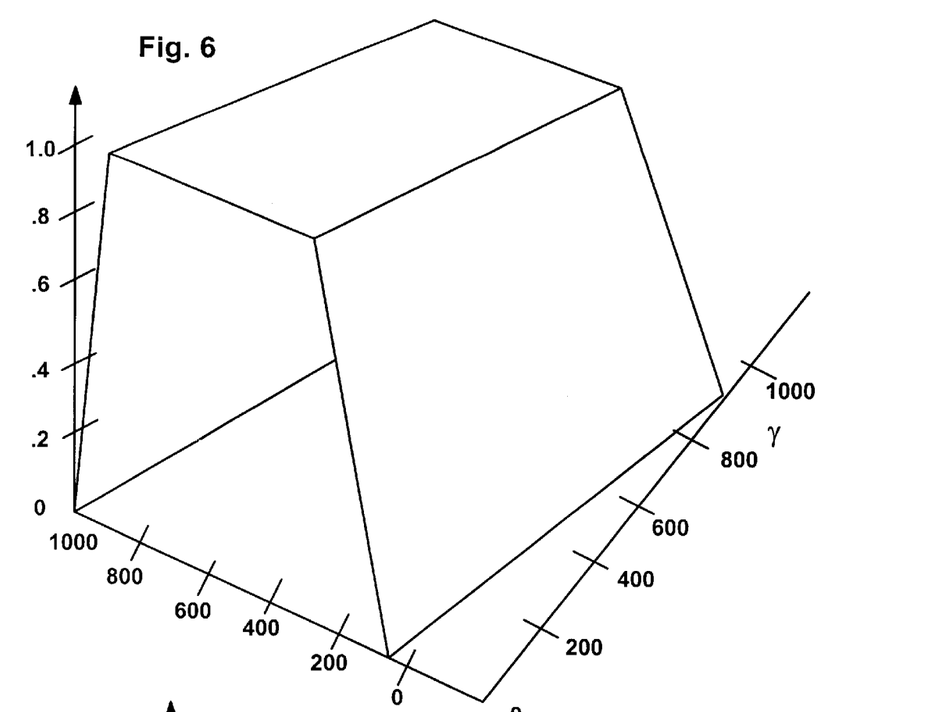
FIG. 6 a three dimensional graph illustrating the summation of weights across a plurality of detector rows after the helical weighting function illustrated in FIG. 5 has been applied.
Figure 7:
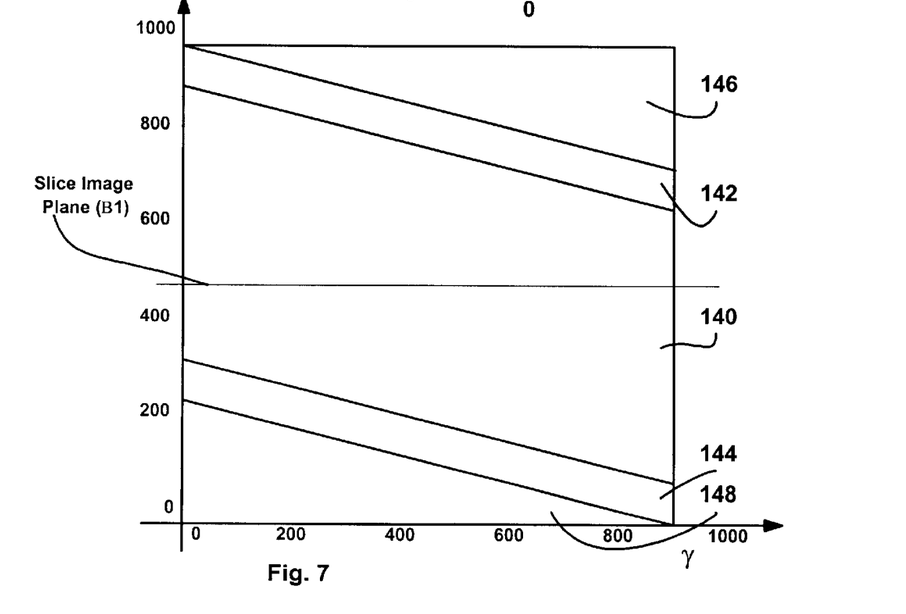
FIG. 7 is a two-dimensional graph corresponding to FIG. 6.
Figure 8:
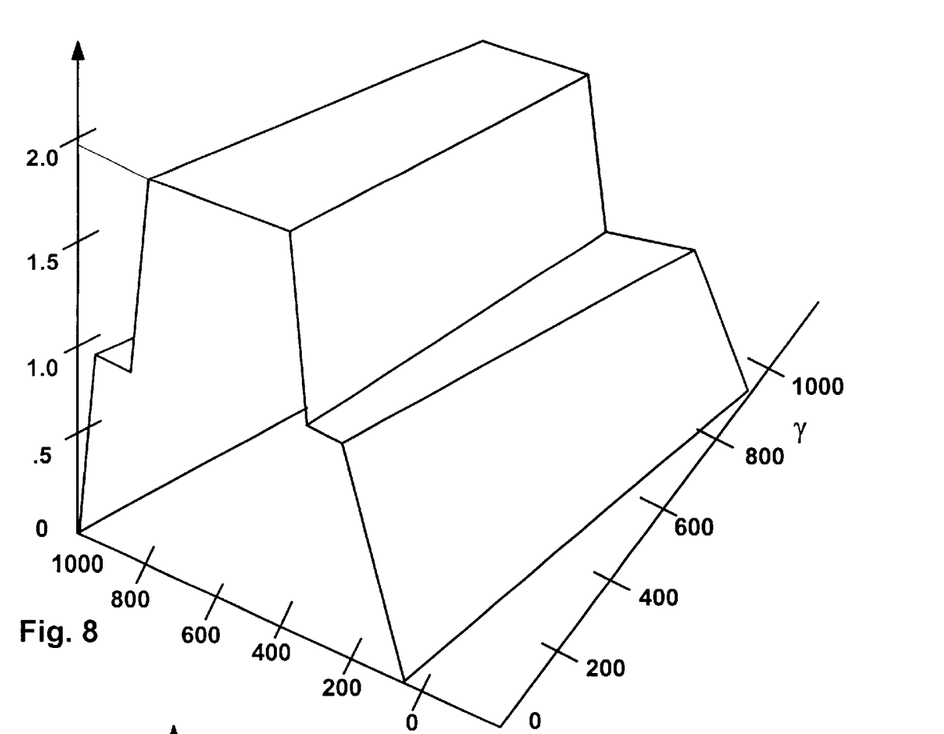
FIG. 8 is similar to FIG. 6 albeit illustrating a three-dimensional graph corresponding to summed weights after both the helical weighting function and a conjugate weighting function have been applied.
Figure 9:
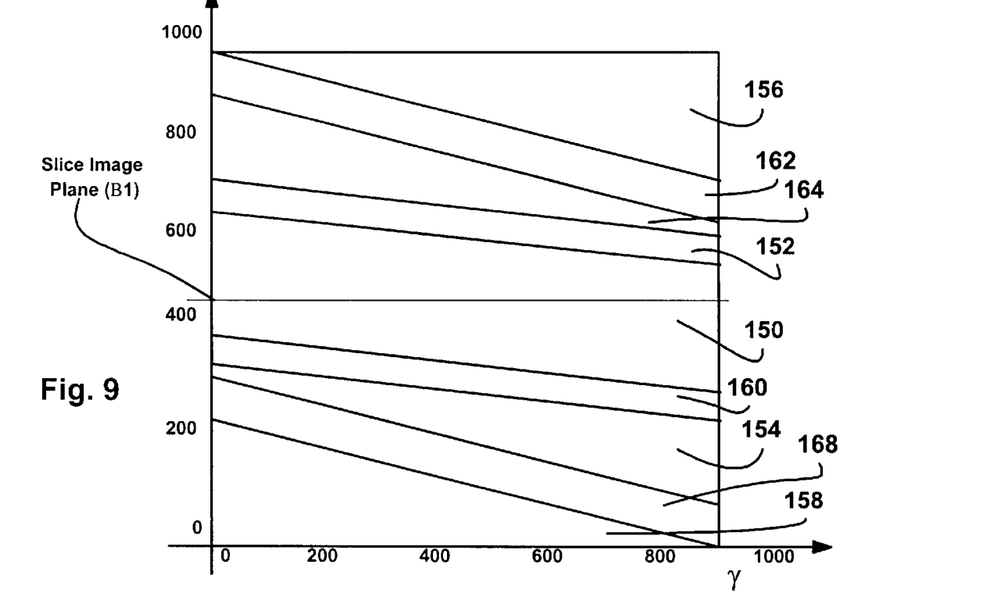
FIG. 9 is a similar to FIG. 7, albeit corresponding to the three-dimensional graph illustrated in FIG. 8.

Referring to FIGS. 8 and 9, three and two dimensional graphs similar to those of FIGS. 6 and 7 are provided, respectively, that show the final weights after combining the conjugate weights and the helical weights. In FIGS. 8 and 9 there are nine separately weighted regions including a region 150 having a weight of two, region 154 having combined weights of one, region 164 having combined weights of one, region 156 having combined weights of zero, region 158 having combined weights of zero, region 162 ramps from zero to one between regions 156 and 164, region 168 ramps from zero to one between regions 158 and 154, region 152 ramps from one to two between regions 164 and 150 and region 160 ramps from one to two between regions 154 and 150. Once again it should be appreciated that the weighting function of FIGS. 8 and 9 is unique.

If the desired slice profile is thicker than the profiles supported by the data and reconstruction algorithms described above, a thicker slice can be derived by summing multiple thin slices within the desired slice profile. If the multiple thin slices by themselves are not of interest, the intermediate step of reconstructing multiple thin slices can be bypassed by performing the corresponding summation early in the projection domain. This reduces the computation load and the image storage load. The resultant weighting functions can be derived by summing corresponding shifted versions of the data planes.

From the preceding description of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used.

To apprise the public of the scope of this invention, the following claims are made.

What is claimed is:

1. An apparatus for use with a CT imaging system including a radiation source and opposed detector mounted to a gantry on opposite sides of an imaging area, the detector including N separate detector rows arranged perpendicular to a translation axis, the apparatus for producing a tomographic slice image through a slice image plane passing through a region of interest (ROI) within an object from a projection data set acquired in a helical scan having a pitch p where the data set includes N separate row data sets corresponding to the N detector rows and each row data set correlates row views with gantry angles, a central angle β within the projection data set essentially aligned with the slice image plane, the apparatus comprising an image reconstructor configured to:

create a separate projection data array for each of the N separate row data sets;

apply a helical weighting function to each of the projection data arrays to generate a separate helical weighted array for each projection data array, the weighting function to be applied to each projection data array being:

$$w_r(\beta, \gamma) = \begin{cases} 0, & \beta > \beta_{r3} \\ 1 - \dfrac{\beta - \beta_{r2}}{\Delta\beta}, & \beta_{r1} \geq \beta > \beta_{r2} \\ 1 + \dfrac{\beta - \beta_{r2}}{\Delta\beta}, & \beta_{r2} \geq \beta \geq \beta_{r1} \\ 0, & \beta < \beta_1 \end{cases}$$

-continued where $\Delta\beta \frac{2\pi}{p}$, $\beta_{r1} = t_g\gamma + r\Delta\beta$, $\beta_{r2} = \beta_{r1} + \Delta\beta$, and $\beta_{r3} = \beta_{r1} + 2\Delta\beta$.

where $t_g$ is a tangent weighting parameter, $\gamma$ is a fan angle within each beam and r is the detector row number having a value between 0 and N−1; and (c) construct a slice image using the helical weighted arrays.

2. The apparatus of claim 1 wherein the reconstructor is further configured to apply a conjugate weighted function to each of the helical weighted arrays thereby generating a conjugate weighted array for each helical weighted array and wherein the reconstructor is configured to construct the slice image using the conjugate weighted arrays.

3. The apparatus of claim 2 wherein the conjugate weighted function includes the following equation:

$$w_c(\beta, \gamma) = \begin{cases} 1 - w_n, & \beta_{nc} \leq \beta < \beta_{nc} + \Delta\beta \\ 2, & \beta_{nc} + \Delta\beta \leq \beta < \beta_{n0} - \Delta\beta \\ 1 - w_0, & \beta_{n0} - \Delta\beta \leq \beta \leq \beta_{n0} \end{cases}$$

where $w_0$ and $w_n$ are helical weighting functions for the first and last detector rows, respectively, and $\beta n_0$ and $\beta n_c$ are conjugate parameters corresponding to the beginning of the first row and the end of the last row, respectively.

4. The apparatus of claim 3 wherein the reconstructor is configured to use the conjugate weighted arrays to generate the slice image by, for each gantry angle within the slice image plane, adding the conjugate weighted arrays corresponding to each detector row and to the gantry angle to generate a combined weighted array for the angle, filtering the combined weighted arrays and then back-projecting the combined weighted arrays.

5. The apparatus of claim 3 wherein the reconstructor is configured to use the conjugate weighted arrays to generate the slice image by, for the conjugate. weighted arrays corresponding to each detector row, filtering and back-projecting the conjugate gated arrays to generate a row specific slice image and then adding the row specific slice images to generate a final slice image within the image plane.

6. The apparatus of claim 1 wherein the reconstructor is further configured to, prior to applying the helical. weighting function to each of the projection data arrays, storing the data arrays in a system memory for reconstructing a plurality of slice images.

7. An apparatus for use with a CT imaging system including a radiation source and opposed detector mounted to a gantry on opposite sides of an imaging area, the source generating a fan beam including rays at varying fan beam angles $\gamma$, the detector including N separate detector rows arranged perpendicular to a translation axis, the apparatus for producing a tomographic slice image through a slice image plane passing through a region of interest (ROI) within an object from a projection data set acquired in a helical scan having a pitch p where the data set includes N separate row data sets corresponding to the N detector rows and each row data set correlates row views with gantry angles, a central angle $\beta$ within the projection data set essentially aligned with the slice image plane, the apparatus comprising an image reconstructor configured to:

create a separate projection data array for each of the N separate row data sets;

apply a helical weighting function to each of the projection data arrays to generate a separate helical weighted array for each projection data array wherein the weighting function corresponding to each row view is dependent on both the gantry angle and the fan angle; and construct a slice image using the helical weighted arrays.

8. The apparatus of claim 7 wherein the reconstructor is further configured to apply a conjugate weighted function to each of the helical weighted arrays thereby generating a conjugate weighted array for each helical weighted array and wherein the reconstructor is configured to construct the slice image using the conjugate weighted arrays.

9. The apparatus of claim 8 wherein the conjugate weighted function includes the following equation:

$$w_c(\beta, \gamma) = \begin{cases} 1 - w_n, & \beta_{nc} \leq \beta < \beta_{nc} + \Delta\beta \\ 2, & \beta_{nc} + \Delta\beta \leq \beta < \beta_{n0} - \Delta\beta \\ 1 - w_0, & \beta_{n0} - \Delta\beta \leq \beta \leq \beta_{n0} \end{cases}$$

where $w_0$ and $w_n$ are helical weighting functions for the first and last detector rows, respectively, and $\beta n_0$ and $\beta n_c$ are conjugate parameters corresponding to the beginning of the first row and the end of the last row, respectively.

10. The apparatus of claim' 9 wherein the reconstructor is configured to use the conjugate weighted arrays to generate the slice image by, for each gantry angle within the slice image plane, adding the conjugate weighted arrays corresponding to each detector row and to the gantry angle to generate a combined weighted array for the angle, filtering the combined weighted arrays and then back-projecting the combined weighted arrays.

11. The apparatus of claim 9 wherein the reconstructor is configured to use the conjugate weighted arrays to generate the slice image by, for the conjugate weighted arrays corresponding to each detector row, filtering and back-projecting the conjugate gated arrays to generate a row specific slice image and then adding the row specific slice images to generate a final slice image within the image plane.

12. A method for use with a CT imaging system including a radiation source and opposed detector mounted to a gantry on opposite sides of an imaging area, the detector including N separate detector rows arranged perpendicular to a translation axis, the method for producing a tomographic slice image through a slice image plane passing through a region of interest (ROI) within an object from a projection data set acquired in a helical scan having a pitch p where the data set includes N separate row data sets corresponding to the N detector rows and each row data set correlates row views with gantry angles, a central angle , within the projection data set essentially aligned with the slice image plane, the method comprising the steps of:

creating a separate projection data array for each of the N separate row data sets;

applying a helical weighting function to each of the projection data arrays generated in step (a) to generate a separate helical weighted array for each projection data array, the weighting function to be applied to each projection data array being:

$$w_r(\beta, \gamma) = \begin{cases} 0, & \beta > \beta_{r3} \\ 1 - \dfrac{\beta - \beta_{r2}}{\Delta \beta}, & \beta_{r1} \geq \beta > \beta_{r2} \\ 1 + \dfrac{\beta - \beta_{r2}}{\Delta \beta}, & \beta_{r2} \geq \beta \geq \beta_{r1} \\ 0, & \beta < \beta_1 \end{cases}$$

where $\Delta\beta \dfrac{2\pi}{p}$, $\beta_{r1} = t_g \gamma + r\Delta\beta$, $\beta_{r2} = \beta_{r1} + \Delta\beta$, and $\beta_{r3} = \beta_{r1} + 2\Delta\beta$.

where $t_g$ is a tangent weighting parameter, $\gamma$ is a fan angle within each beam and r is the detector row number having a value between 0 and N−1; and constructing a slice image using the helical weighted arrays.

13. The method of claim 12 further including the step of applying a conjugate weighted function to each of the helical weighted arrays thereby generating a conjugate weighted array for each helical weighted array and wherein the step of constructing includes constructing the slice image using the conjugate weighted arrays.

14. The method of claim 13 wherein the conjugate weighted function includes the following equation:

$$w_c(\beta, \gamma) = \begin{cases} 1 - w_n, & \beta_{nc} \leq \beta < \beta_{nc} + \Delta\beta \\ 2, & \beta_{nc} + \Delta\beta \leq \beta < \beta_{n0} - \Delta\beta \\ 1 - w_0, & \beta_{n0} - \Delta\beta \leq \beta \leq \beta_{n0} \end{cases}$$

where $w_0$ and $w_n$ are helical weighting functions for the first and last detector rows, respectively, and $\beta n_0$ and $\beta n_c$ are conjugate parameters corresponding to the beginning of the first row and the end of the last row, respectively.

15. The method of claim 14 wherein the step of using the conjugate weighted arrays to generate the slice image includes, for each gantry angle within the slice image plane, adding the conjugate weighted arrays corresponding to each detector row and to the gantry angle to generate a combined weighted array for the angle, filtering the combined weighted arrays and then back-projecting the combined weighted arrays.

16. The method of claim 14 wherein the step of using the conjugate weighted arrays to generate the slice image includes, for the conjugate weighted arrays corresponding to each detector row, filtering and back-projecting the conjugate gated arrays to generate a row specific slice image and then adding the row specific slice images to generate a final slice image within the image plane.

17. The method of claim 12 further including the step of, prior to applying the helical weighting function to each of the projection data arrays, storing the data arrays in a system memory for reconstructing a plurality of slice images.

18. A method for use with a CT imaging system including a radiation source and opposed detector mounted to a gantry on opposite sides of an imaging area, the source generating a fan beam including rays at varying fan beam angles $\gamma$, the detector including N separate detector rows arranged perpendicular to a translation axis, the method for producing a tomographic slice image through a slice image plane passing through a region of interest (ROI) within an object from a projection data set acquired in a helical scan having a pitch p where the data set includes N separate row data sets corresponding to the N detector rows and each row data set correlates row views with gantry angles, a central angle $\beta$ within the projection data set essentially aligned with the slice image plane, the method comprising the steps of:

creating a separate projection data array for each of the N separate row data sets;

applying a helical weighting function to each of the projection data arrays to generate a separate helical weighted array for each projection data array wherein the weighting function corresponding to each row view is dependent on both the gantry angle and the fan angle; and constructing a slice image using the helical weighted arrays.

19. The method of claim 18 further including the step of applying a conjugate weighted function to each of the helical weighted arrays thereby generating a conjugate weighted array for each helical weighted array and wherein the step of constructing the slice image includes using the conjugate weighted arrays.

20. The method of claim 19 wherein the conjugate weighted function includes the following equation:

$$w_c(\beta, \gamma) = \begin{cases} 1 - w_n, & \beta_{nc} \leq \beta < \beta_{nc} + \Delta\beta \\ 2, & \beta_{nc} + \Delta\beta \leq \beta < \beta_{n0} - \Delta\beta \\ 1 - w_0, & \beta_{n0} - \Delta\beta \leq \beta \leq \beta_{n0} \end{cases}$$

where $w_0$ and $w_n$ are helical weighting functions for the first and last detector rows, respectively, and $\beta n_0$ and $\beta n_c$ are conjugate parameters corresponding to the beginning of the first row and the end of the last row, respectively.

* * * * *

UNITED STATES PATENT AND TRADEMARK OFFICE
CERTIFICATE OF CORRECTION

PATENT NO. : 6,522,714 B1 Page 1 of 1
DATED : February 18, 2003
INVENTOR(S) : Sharon Wang et al.

It is certified that error appears in the above-identified patent and that said Letters Patent is hereby corrected as shown below:

Column 8,
Insert between lines 37 & 38 -- p=d/s --.

Column 11,
Line 8, "$\beta_2$" should be -- $\beta_{r2}$ --.
Line 45, "conjugate." should be -- conjugate --.
Line 52, "helical." should be -- helical --.

Signed and Sealed this

Eighth Day of July, 2003

JAMES E. ROGAN
*Director of the United States Patent and Trademark Office*